United States Patent [19]

Down

[11] 4,317,659
[45] Mar. 2, 1982

[54] PRODUCTION OF HYDROGEN, ACETYLENE AND AMMONIA GASES FROM LITHIUM REACTION WITH HYDROCARBON MATERIALS

[75] Inventor: Michael G. Down, Plum Borough, Pa.

[73] Assignee: Westinghouse Electric Corp., Pittsburgh, Pa.

[21] Appl. No.: 114,879

[22] Filed: Jan. 24, 1980

[51] Int. Cl.³ .............................................. C10J 3/00
[52] U.S. Cl. ........................................ 48/209; 48/210; 48/216; 423/439; 423/646; 585/534
[58] Field of Search ............... 48/216, 209, 210, 59, 48/47, 38; 585/534; 423/439, 441, 442, 353, 646

[56] References Cited

U.S. PATENT DOCUMENTS

| 889,124 | 5/1908 | Hartenstein | 423/442 |
|---|---|---|---|
| 2,950,956 | 8/1960 | McKinley et al. | 423/442 |
| 3,460,925 | 8/1969 | Mitchell, Jr. | 48/216 |
| 4,009,219 | 2/1977 | Tamers | 423/439 |
| 4,028,068 | 6/1977 | Kiener | 48/209 |
| 4,128,624 | 12/1978 | Tamers | 423/439 |
| 4,137,295 | 1/1979 | Tamers | 423/442 |
| 4,184,852 | 1/1980 | Russ | 423/439 |

*Primary Examiner*—S. Leon Bashore
*Assistant Examiner*—Michael L. Goldman
*Attorney, Agent, or Firm*—D. P. Cillo

[57] ABSTRACT

A method of producing $H_2$ and $C_2H_2$ gases comprises the steps of drying a hydrocarbon biomass material to remove water without carbonization, reacting the dried hydrocarbon biomass with a stoichiometric excess of molten lithium metal to produce lithium salts comprising LiH and $Li_2C_2$ and then hydrolyzing the lithium salts to produce a gaseous mixture comprising $H_2$ and $C_2H_2$.

10 Claims, 1 Drawing Figure

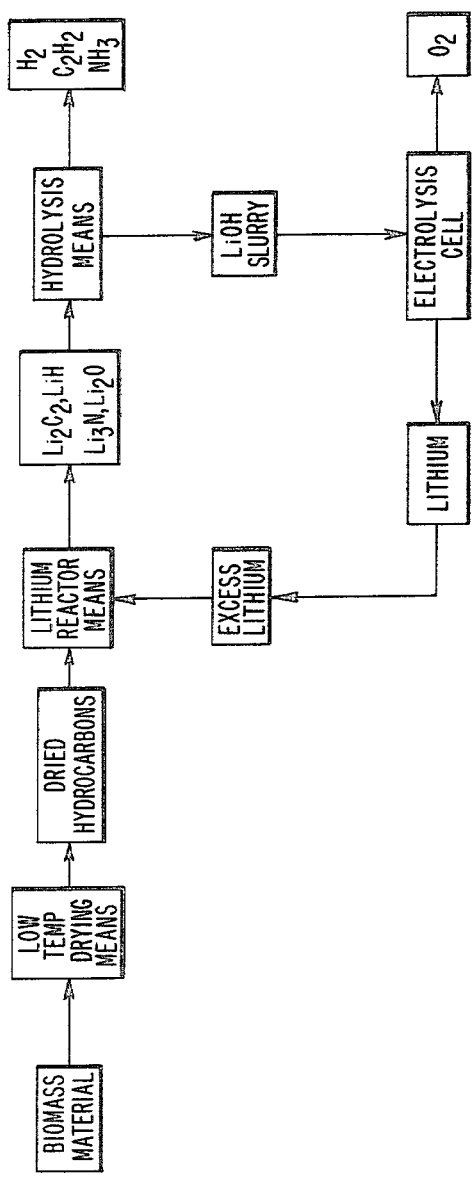

PRODUCTION OF HYDROGEN, ACETYLENE AND AMMONIA GASES FROM LITHIUM REACTION WITH HYDROCARBON MATERIALS

BACKGROUND OF THE INVENTION

While precious fossil fuels are being steadily depleted to provide electricity and petrochemicals, biomass materials, such as household wastes, animal wastes, field crop wastes, forestry wastes, etc. are produced in enormous amounts, and constitute a tremendous waste of potential energy.

In an attempt to utilize these biomass materials, Tamers, in U.S. Pat. No. 4,009,219, in one embodiment of his invention, completely carbonizes biomass materials at over 1,000° C., for at least 30 minutes in the absence of air, driving off oxygen, nitrogen and hydrogen gas, to provide an essentially pure carbon char. This pure carbon char is then reacted with less than a stoichiometric amount of lithium, sodium, potassium or cesium in the form of the metal, hydroxide or oxide, at over about 500° C. This produces substantially all metal carbide solids, which are then hydrolized to produce acetylene. All reactions of metal with oxygen, water or nitrogen are avoided. Following acetylene production, the metal is recovered by a variety of means.

This process, however, when converting biomass to pure carbon char, wastes hydrogen, oxygen and nitrogen gases, which are considered undesirable products capable of consuming lithium. The process also requires a tremendous input of energy in the form of heat, to completely carbonize the biomass at 1,000° C. for 30 minutes. What is needed is a new and improved process that can directly produce a variety of energy useful gases, particularly hydrogen, from biomass materials, without excessive use of heat energy.

SUMMARY OF THE INVENTION

It has been discovered that the above-described need can be met by a process comprising the steps of: (1) drying hydrocarbon biomass material in air, preferably at a temperature of between about 25° C. to about 65° C., to provide dried hydrocarbon biomass, (2) reacting the resulting hydrocarbon materials, containing major amounts of hydrogen as well as carbon atoms, and which may contain minor amounts of nitrogen, with a stoichiometric excess of molten lithium metal, in a lithium reactor means, in an absence of air and moisture, at a temperature of between about 300° C. to about 1,200° C., to provide lithium salt compounds such as LiH, $Li_2C_2$, and possibly $Li_3N$ and $Li_2O$, and (3) hydrolyzing the lithium salts at a low temperature, to provide a variety of gases, such as hydrogen, acetylene, and possibly ammonia. A lithium hydroxide slurry can be recovered from the hydrolysis step and converted to lithium metal by a variety of means, for recycle to the lithium reactor means.

Thus, major amounts of hydrogen gas are generated and minimal heat is expended in the process prior to lithium reaction. The process can also produce substantial amounts of ammonia, which is valuable in producing fertilizer. The use of excess lithium metal is essential to the process, to prevent formation of complex lithium species which do not readily hydrolyze to provide useful fuel gases.

BRIEF DESCRIPTION OF THE DRAWING

For a better understanding of the invention, reference may be made to the preferred embodiments, exemplary of the invention, shown in the accompanying drawing which shows a flow chart of one embodiment of the method of this invention.

DESCRIPTION OF THE PREFERRED EMBODIMENTS

The hydrocarbon biomass starting material for the process of this invention, shown in the Drawing, is defined herein as comprising, for example, field crop wastes, forestry material wastes including leaves, bark and wood chips, househould wastes such as garbage, sewage and newspapers, animal wastes such as manure, low grade coal such as that having high sulfur or residual ash content, and waste plastics such as polyethylene or polypropylene discard, among others. These biomass materials, either alone or in mixtures, are dried in a low temperature drying means in the presence of air, at a temperature and for a time effective to remove substantially all water, without destructive heating or carbonization, and without driving off any substantial amount of hydrogen, oxygen or nitrogen gas. It is essential to the process that any hydrogen, oxygen and nitrogen remain in the dried biomass hydrocarbon material, so that hydrogen and ammonia gases are yielded as a final product. The drying temperature range is preferably between about 25° C. to about 65° C., for between about ½ hour to about 6 hours. Low cost energy sources, such as solar heat, can thus be useful.

The dried, non-carbonized, biomass hydrocarbon material is then fed into a heated, sealed, leak free, lithium reactor means, which is usually made from a non-reactive material such as stainless steel. Molten lithium is contained in the vessel, which also usually contains an inert atmosphere, such as argon or helium, over the molten metal. This reactor vessel will usually have a mechanical stirrer, or a rotating magnet disposed under the vessel, effective to cause stirring of the lithium metal in the vessel. Air and moisture are excluded from the vessel which operates at a temperature of between about 300° C. to about 1,200° C. The exothermic interaction in the lithium reactor, which helps maintain sufficient reactor temperature, comprises the following chemical reactions:

| | HEAT OF REACTION |
|---|---|
| Li + H = LiH (lithium hydride) | 91.2 kJ $mol^{-1}$, |
| Li + C = $Li_2C_2$ (lithium acetylide) | 59.4 kJ $mol^{-1}$, |
| Li + N = $Li_3N$ (lithium nitride) | 198.6 kJ $mol^{-1}$, and |
| Li + O = $Li_2O$ (lithium oxide) | 587.9 kJ $mol^{-1}$ |

Liquid lithium (m.p.=180° C.) provides a highly reactive, relatively low temperature reducing medium. In this environment, heteroatomic organic and inorganic molecules are readily degraded to their constituent elements, which in turn react with lithium, to form the binary lithium salts described above. The usual mole % ratio of salts will be between about 50 to 80 mole % LiH, about 20 to 50 mole % $Li_2C_2$ and up to about 10 mole % $Li_3N$ and $Li_2O$. In some instances no $Li_3N$ or $Li_2O$ will be produced, such as when polyethylene is used as the biomass. Lithium metal is unique among the alkali metals in reacting directly with carbon and nitrogen in this manner, and is the sole metal useful in the reactor means.

The resulting lithium salts are highly stable, and it is this great stability which provides the driving force for the dissociation of the original molecule. The stability of these salts, and use of the excess stoichiometric amounts of lithium, precludes the formation of heteroatomic anions, such as $Li_2SO_4$, $LiNO_3$, $LiCO_3$, which do not readily hydrolyze to provide useful fuel gases. By "stoichiometric excess of lithium", is meant an amount of from 2 to 200 mole %, preferably 75 to 125 mole %, of Li in excess of that required to completely react with all the total H, C, O and N present in the biomass. The reaction, accompanied by constant stirring, is completed in about ¾ hour to 1½ hours, preferably at a temperature of between about 700° C. to 900° C., resulting in a top liquid phase consisting of molten lithium, and a bottom solid reaction product phase usually consisting of the $Li_2C_2$, LiH, $Li_3N$ and $Li_2O$ salts. The excess lithium is then cooled to about 300° C. before being drawn off, and then the reaction product solids are allowed to cool. The cooled reaction product solids are then either transferred to another vessel for hydrolysis, or left in place so that hydrolysis is accomplished in the same vessel.

The key to the liberation of valuable gaseous fuels, or their synthesis base chemicals from organic materials, lies in the room temperature hydrolysis of the binary reaction product solids by the following chemical reactions:

|  | HEAT OF REACTION |
|---|---|
| $LiH + H_2O = LiOH + H_2$ (hydrogen gas) | 108.4 kJ mol$^{-1}$, |
| $Li_2C_2 + 2H_2O = 2LiOH + C_2H_2$ (acetylene gas) | 113.0 kJ mol$^{-1}$, |
| $Li_3N + 3H_2O = 3LiOH + NH_3$ (ammonia gas) and formation of a lithium containing slurry: | 446.0 kJ mol$^{-1}$, |
| $Li_2O + H_2O = 2LiOH$ (to be recycled) | 131.7 kJ mol$^{-1}$, |

These reactions proceed vigorously at room temperature and are accompanied by the evolution of heat in addition to the gaseous products.

These product gases provide a variety of possible uses. Acetylene and hydrogen are combustible, and in addition hydrogen has attracted considerable attention as an alternative energy source for aircraft and automobiles in the late 1980's. They can also be used as synthesis base materials. Acetylene readily undergoes addition or hydration reactions and can be converted to, aldehydes, ketones and alcohols. Ammonia finds use in refining, explosives, refrigeration and chemicals. Ammonia is also used in large amounts in the fertilizer industry, and is generally produced by the steam/methane process, which is very energy intensive and is responsible for consumption of 3% of America's annual natural gas resources.

The ratio of products would depend on the particular starting material chosen. The usual mole % ratio of gases will be between about 50 to 80 mole % hydrogen, about 20 to 50 mole % acetylene and up to about 10 mole % ammonia i.e., from 0% to about 10% ammonia. The thermal losses can be minimized by using the heat evolved in the hydrolysis to help dry the initial biomass. These product gases can be easily separated by methods well known in the art, such as suitable micro porous membrane separation techniques, preferential dissolution, various cryogenic techniques and the like.

Reprocessing of the lithium hydroxide to produce lithium metal and oxygen is achieved, for example, by electrolysis of fused chloride at about 410° C., after a suitable conversion step, as shown by the following chemical reactions:

$2LiOH + CO_2 = Li_2CO_3 + H_2O$

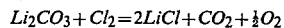
$Li_2CO_3 + Cl_2 = 2LiCl + CO_2 + \tfrac{1}{2}O_2$

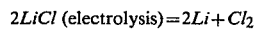
$2LiCl$ (electrolysis) $= 2Li + Cl_2$

The overall reaction is:

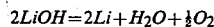
$2LiOH = 2Li + H_2O + \tfrac{1}{2}O_2$

Each pound of lithium metal recycled in this way would require about 1750 amp-hours and a sufficient voltage to dissociate the chloride, approximately 2.5 volts. Any other method known to the art could of course be used to produce lithium metal from the hydroxide, to close the biomass/lithium cycle.

I claim:

1. A method of producing a gaseous mixture comprising $H_2$ and $C_2H_2$, comprising the steps of:
   (A) providing a non-carbonized hydrocarbon biomass waste material, and then
   (B) drying the hydrocarbon biomass waste material at a temperature of up to about 65° C. for a time effective to remove substantially all water, without carbonization, to provide a dried non-carbonized hydrocarbon biomass waste material containing major amounts of H and C atoms, where no substantial amount of hydrogen, oxygen or nitrogen gas is driven off from the hydrocarbon biomass material, and then
   (C) reacting the dried, non-carbonized hydrocarbon containing biomass waste material with a stoichiometric excess of molten lithium metal, at a temperature over about 300° C. in the absence of air and moisture, to produce a product mixture comprising lithium salts: LiH and $Li_2C_2$, and then
   (D) hydrolyzing the lithium salts to produce a gaseous product mixture comprising $H_2$ and $C_2H_2$.

2. The method of claim 1, wherein the biomass hydrocarbon material is dried for up to about 6 hours in step (B).

3. The method of claim 1, wherein the biomass hydrocarbon material is dried in air at a temperature of between about 25° C. to about 65° C. for between about ½ hour to about 6 hours in step (B).

4. The method of claim 1, wherein the mole % ratio of LiH to $Li_2C_2$ in step (C) is about 50 mole % to 80 mole % LiH to about 20 mole % to 50 mole % $Li_2C_2$.

5. The method of claim 1, wherein the reaction product mixture in step (C) also contains up to 10 mole % $Li_3N$ and up to 10 mole % $Li_2O$.

6. The method of claim 1, wherein the mole % ratio of $H_2$ to $C_2H_2$ in step (D) is about 50 to 80 mole % $H_2$ to about 20 to 50 mole % $C_2H_2$.

7. The method of claim 1, wherein the gaseous product mixture in step (D) also contains up to about 10 mole % $NH_3$.

8. The method of claim 1, wherein, during hydrolysis, LiOH is also produced, and said LiOH is converted to Li metal and recycled back to step (C).

9. The method of claim 1, wherein the biomass is selected from the group of materials consisting of household wastes, animal wastes, field crop wastes, forestry wastes, low grade coal, waste plastics, and their mixtures, and where the reaction in step (C) is at a temperature of between about 300° C. and about 1,200° C.

10. The method of claim 8, wherein LiOH is reacted to form lithium chloride, which is then electrolyzed to provide Li metal and oxygen.

* * * * *